United States Patent [19]

Andrews

[11] 4,245,986
[45] Jan. 20, 1981

[54] ORTHODONTIC FACE BOW

[75] Inventor: Lawrence F. Andrews, San Diego, Calif.

[73] Assignee: "A"-Company, Inc., San Diego, Calif.

[21] Appl. No.: 31,276

[22] Filed: Apr. 18, 1979

[51] Int. Cl.³ .............................................. A61C 7/00
[52] U.S. Cl. ...................................................... 433/5
[58] Field of Search ................................ 433/19, 22, 5

[56] References Cited

U.S. PATENT DOCUMENTS

| | | |
|---|---|---|
| 721,655 | 3/1903 | Angle ........................................ 433/5 |
| 1,044,764 | 11/1912 | Federspiel ............................... 433/22 |

Primary Examiner—Robert Peshock
Attorney, Agent, or Firm—Townsend & Townsend

[57] ABSTRACT

An improved orthodontic face bow which facilitates the making of a secondary orthodontic correction in addition to the primary correction provided by a conventional face bow is disclosed. An armature projects vertically from the arch member of the face bow. The armature extends from a position proximate the exterior surface of the posterior teeth of one level, usually the upper teeth, to a position proximate the exterior surface of the posterior teeth of the other, usually lower level. An engaging surface is provided at the distal end of the armature. A tension member such as a rubber band is used to interconnect the engaging surface of the armature and the anterior teeth of said other level. The tension member provides a rearwardly directed force on the anterior teeth at the level of the engaging means to induce an orthodontic correction on the anterior teeth of said other level.

6 Claims, 2 Drawing Figures

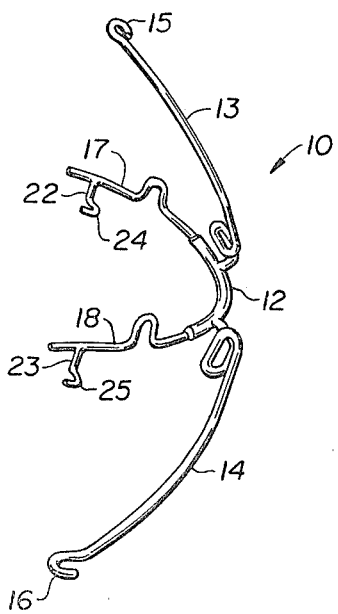
FIG._1.
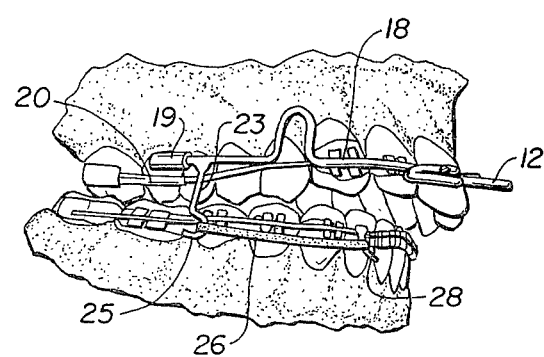
FIG._2.

ORTHODONTIC FACE BOW

BACKGROUND OF THE INVENTION

The present invention relates to orthodontic face bows, and in particular to an orthodontic face bow which provides a secondary orthodontic correction to the anterior lower teeth of the wearer.

Orthodontic face bows, such as that illustrated in the patent to Case, U.S. Pat. No. 862,881, are used to make certain types of orthodontic corrections in which an outside source of a rearwardly directed force is desired. The face bow includes a frame which fits around the face of the wearer and connects to a headstrap which biases the frame rearwardly relative to the head of the wearer. The frame connects to arch members inside the wearer's mouth which fit around the exterior of the upper teeth (or, on rare occasions, the lower teeth) of the wearer and engage buccal tubes fixed to the posterior upper teeth. The face bow thus provides a rearward force on the posterior upper teeth of the wearer to correct a malocclusion without unwanted reactionary forces on other portions of the mouth.

In many situations, it is also desirable to use the face bow for the secondary purpose of providing a rearwardly directed force on the anterior lower teeth of the wearer. This is now usually done in a jerry-rig style by simply hooking rubber bands from the buccal tubes engaged by the face bow to braces attached to the anterior lower teeth. The rubber bands are tension members which induce the desired rearwardly directed force on the anterior lower teeth.

The problem with using currently available face bows to provide a secondary correction for the anterior lower teeth as discussed above is that the force provided by the tension member is not precisely rearwardly directed. Since the tension member runs from the posterior upper teeth to the anterior lower teeth, a downward force component is exerted on the posterior upper teeth, and an upward force component is exerted on the anterior upper teeth. These vertical force components are normally termed "extrusion vectors", and can cause unwanted tooth movement which interferes with the desired orthodontic correction.

U.S. Pat. No. 3,131,953 to Asher illustrates the use of an upturned hook on the arch member of the face bow to facilitate attachment of a rubber band thereto. However, as illustrated in the Asher patent, rubber bands emanating from such a hook should only be connected to the anterior upper teeth—connection to the anterior lower teeth would result in the same unwanted extrusion vectors discussed above.

SUMMARY OF THE INVENTION

The present invention provides an armature which projects vertically from the arch member of a face bow. The armature extends from a position proximate the exterior surface of the posterior teeth of one level, usually the upper teeth, to a position proximate the exterior surface of the posterior teeth of the other, usually lower, level. An engaging surface is provided at the distal end of the armature. A tension member such as a rubber band is used to interconnect the engaging surface of the armature and the anterior teeth of said other level to provide a rearwardly directed force on the anterior teeth at the level of the engaging means to induce an orthodontic correction.

In the present invention, the tension member runs along the exterior surface of one level of teeth from posterior to anterior. Since the tension member can only exert forces along its axis, the forces exerted when the present invention is employed are entirely rearwardly directed in the plane of that level of teeth. No extrusion vector is created which would result in undesirable vertical forces on the teeth and interfere with the desired orthodontic correction.

The novel features which are chracteristic of the invention, as to organization and method of operation, together with further objects and advantages thereof will be better understood from the following description considered in connection with the accompanied drawings which a preferred embodiment of the invention is illustrated by way of example. It is to be expressly understood, however, that the drawings are for the purpose of illustration and description only and are not intended as a definition of the limits of the invention.

BRIEF DESCRIPTION OF THE DRAWINGS

FIG. 1 is a perspective view of a face bow modified according to the teachings of the present invention;

FIG. 2 is a side elevation view of the face bow of FIG. 1 within the mouth of wearer.

DESCRIPTION OF THE PREFERRED EMBODIMENT

A face bow 10 incorporating the features of the present invention is illustrated by way of reference to FIG. 1. Face bow 10 includes a conventional frame 12 having members 13, 14 extending laterally and adapted to partially circumscribe the face of the wearer. Hooks 15, 16 are provided at the ends of members 13, 14 to attach to a head strap which passes around the back of the wearer's head. Arch members 17, 18 emanate from frame 12 and fit within the mouth of the wearer.

As illustrated in FIG. 2, each arch member such as 18 engages a buccal tube 19 fixed to the posterior upper teeth of the wearer. Buccal tube 19 is connected to conventional braces 20. A rearward force is exerted on frame 12 by the head strap passing around the head of the wearer, and this rearward force is transmitted to the posterior upper teeth of the wearer through buccal tubes 19. Face bow 10 thus applies a rearward force on the posterior upper teeth to correct a malocclusion.

The present invention provides a pair of armatures 22, 23 which depend from arch members 17, 18. As illustrated in FIG. 2, each armature such as 23 depends from a position at the exterior of the posterior upper teeth to the exterior of the posterior lower teeth. Rearwardly opening hooks 24, 25 are formed at the lower end of armatures 22, 23 to provide an engaging surface.

A rubber band 26 or other type of tension member is used to connect the hook 25 in each armature such as 23 to the anterior lower teeth. A hook such as 28 can be attached to the anterior lower teeth to facilitate attachment of rubber band 26. A similar rubber band is used to connect hook 24 on armature 22 to the anterior lower teeth at the other side of the mouth.

A tension member such as rubber band 26 is only able to transmit forces along its axis. As illustrated in FIG. 2, the present invention provides that rubber band 26 run along the exterior surface of the lower teeth. In this fashion, the force exerted on the anterior lower teeth by rubber band 26 is directed rearwardly, and no vertical forces are imposed on these teeth. The reaction to this force is provided by frame 12 and a headstrap, and unwanted vertical forces (extrusion vectors) are not exerted on any portion of the mouth.

While a preferred embodiment of the present invention has been illustrated in detail, it is apparent that modifications and adaptations of that embodiment will occur to those skilled in the art. For example, if the face bow attaches to the lower teeth, as is sometimes the case, the armatures would project upwardly to a position proximate the exterior surface of the upper teeth. However, it is to be expressly understood that such modifications and adaptations are within the spirit and scope of the present invention, as set forth in the following claims.

What is claimed is:

1. In an orthodontic face bow that includes an arch member adapted to fit inside a wearer's mouth and engage the posterior teeth of a first level thereof on each side of the mouth, frame means attached to said arch member, and means for biasing said frame means to apply a rearwardly directed force on the posterior teeth of said first level and induce an orthodontic correction, the improvement comprising armature means extending from a position on said arch member approximate the posterior teeth of said first level to a distal end, the distal end having means defining a first engaging surface and adapted to be approximate the exterior surface of the posterior teeth of a second level of teeth, a second engaging surface means attached to anterior teeth of said second level so that when a tension member is engaged between said first and second engaging surface means, there will be provided a rearwardly directed force on said anterior teeth of said second level generally parallel to said second level of teeth, to accomplish a further orthodontic correction.

2. A face bow as recited in claim 1 wherein said armature means includes a pair of armatures located on opposite sides of the wearer's mouth, each armature having an engaging surface at its distal end.

3. A face bow as recited in claim 1 wherein the engaging surface comprises a rearwardly opening hook-shaped member.

4. A face bow as recited in claim 1 wherein the tension member comprises a rubber band.

5. A face bow as recited in claim 1 wherein said first level is the upper layer of teeth, and said second level is the lower layer of teeth.

6. An improved orthodontic face bow for use with upper and lower braces on the upper and lower teeth of a wearer, the lower braces having a pair of hooks adjacent the anterior lower teeth for engagement with a tension member, said face bow being of the type having a generally U-shaped arch member for engagement with the upper braces adjacent the posterior upper teeth and a frame attached to the arch member adjacent to the anterior upper teeth and extending outside the wearer's mouth to at least partially circumscribe the wearer's face, the improvement comprising:

a pair of downwardly extending armatures attached to the posterior portions of the arch member adjacent the exterior surface of the posterior upper teeth;

said armatures each having a hook portion at their distal ends adjacent the exterior surface of the posterior lower teeth to position the tension member between the hook portions of the armatures and the hooks on the lower braces generally parallel to the lower braces.

* * * * *